(12) United States Patent
AlGhamdi

(10) Patent No.: US 8,187,292 B2
(45) Date of Patent: May 29, 2012

(54) SURGICAL SKIN PUNCH APPARATUS

(76) Inventor: Khalid M. AlGhamdi, Riyadh (SA)

( * ) Notice: Subject to any disclaimer, the term of this patent is extended or adjusted under 35 U.S.C. 154(b) by 389 days.

(21) Appl. No.: 12/507,102

(22) Filed: Jul. 22, 2009

(65) Prior Publication Data

US 2011/0022068 A1    Jan. 27, 2011

(51) Int. Cl.
*A61B 17/32* (2006.01)
(52) U.S. Cl. .......................... 606/167; 604/22
(58) Field of Classification Search .......... 606/167, 606/133, 184, 79, 168, 170; 604/22, 46; 600/565

See application file for complete search history.

(56) References Cited

U.S. PATENT DOCUMENTS 5,922,000 A * 7/1999 Chodorow ................. 606/167

OTHER PUBLICATIONS

Rubenstein, Richard, Dermal and Subcutaneous Tumors, 1996, pp. 465-473, New York.
Gupta, Somesh; Pandhi, Roma; Kumar, Bhushan, "Pot-lid" technique for aesthetic removal of small lipoma on the face, International Journal of Dermatology, 2001, pp. 420-424.
Christenson, Leslie; Petterson, James; Davis, David, Surgical Pearl: Use of the cutaneous punch for the removal of lipomas, American Academy of Dermatology, 2000, p. 675-676.

* cited by examiner

*Primary Examiner* — Victor Nguyen
(74) *Attorney, Agent, or Firm* — Neustel Law Offices

(57) ABSTRACT

A surgical skin punch apparatus to excise subcutaneous abnormalities and allow for efficient resealing of the skin surface. The surgical skin punch apparatus generally includes an elongated handle and a cutting member, wherein the cutting member extends from the elongated handle. The cutting member includes a C-shape to form a pivotal skin fragment to access subcutaneous material beneath. A method of using the apparatus is also described.

5 Claims, 9 Drawing Sheets

SURGICAL SKIN PUNCH APPARATUS

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to a surgical instrument and more specifically it relates to a surgical skin punch apparatus to excise subcutaneous abnormalities and allow for efficient resealing of the skin surface.

2. Description of the Related Art

Any discussion of the related art throughout the specification should in no way be considered as an admission that such related art is widely known or forms part of common general knowledge in the field.

Subcutaneous abnormalities, such as lipomas, cysts, lesions, etc., that desire removal are often surgically removed using various types of tools. Often times, a "free hand" scalpel or a circular-blade punch is used to create a surgical incision in the skin about one-half the size of the tumor or other mass that is desired to be removed. The removal of the tumor through the small incision or punch decreases the size of the resulting scar, but does not eliminate it completely. In addition, when using the "free hand" approach the resulting scar can often times be uneven or appear deformed.

When using a circular-blade punch, one method is to discard of the circular skin fragment and leave the site to heal. However, this method generally results in a larger than necessary scar and may be disfavored by patients. Another method is to replace the circular skin fragment back over the defect.

However, limitations of this technique include the possibility that the circular skin fragment may not heal flush with the surrounding skin and thus result in a depressed or elevated scar, or the possibility that blood will not adequately flow to the replaced circular skin fragment which might lead to necrosis and scarring. Because of the inherent problems with the related art, there is a need for a new and improved surgical skin punch apparatus to excise subcutaneous abnormalities and allow for efficient resealing of the skin surface.

BRIEF SUMMARY OF THE INVENTION

A system to excise subcutaneous abnormalities and allow for efficient resealing of the skin surface. The invention generally relates to a surgical instrument which includes an elongated handle and a cutting member including a plurality of cutting edges, wherein the cutting member extends from the elongated handle. The cutting member is comprised of a C-shape to form a pivotal skin fragment to access subcutaneous material beneath. A method of using the apparatus is also described.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
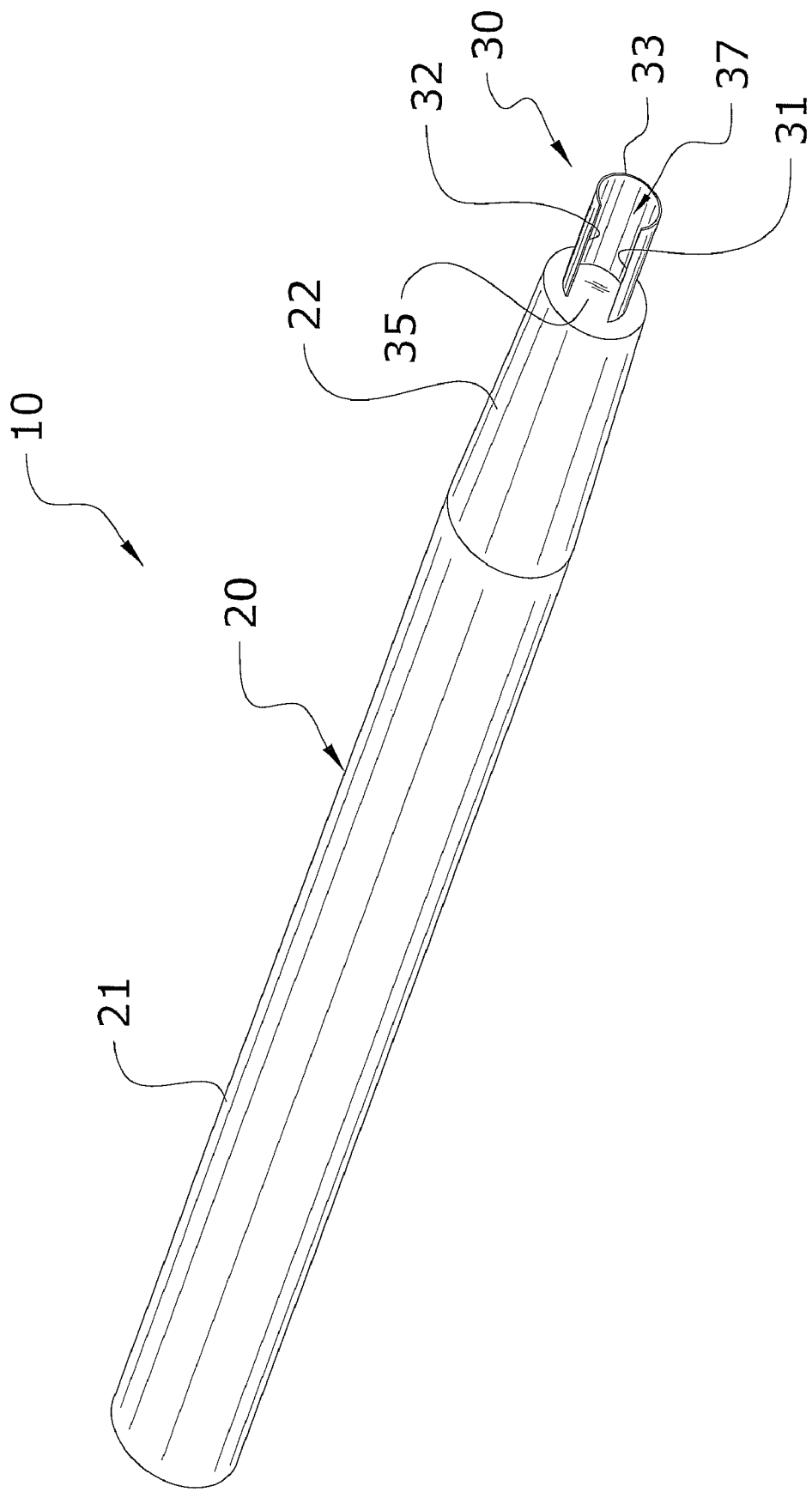
FIG. 1 is an upper perspective view of the present invention.
Figure 2:
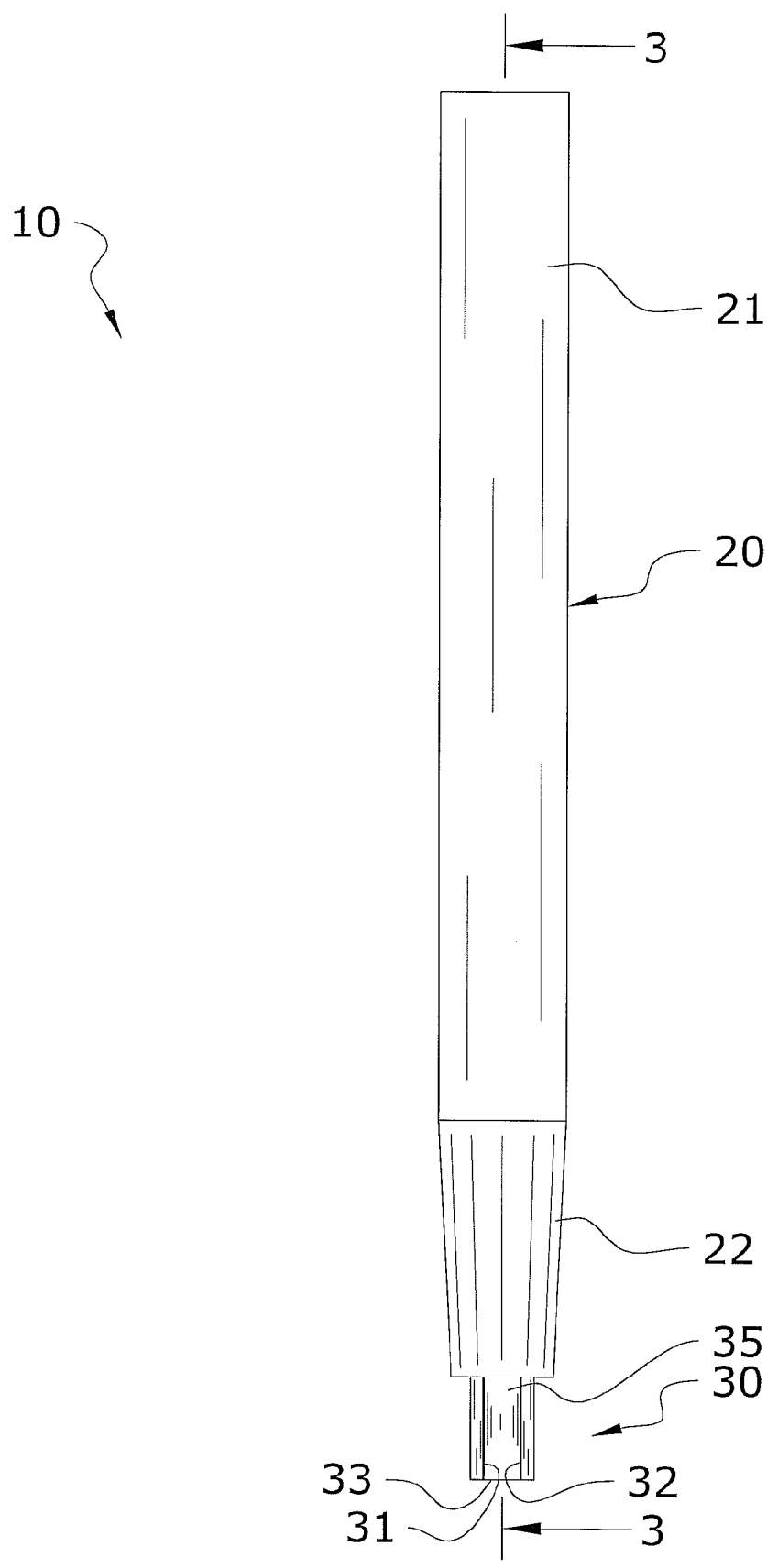
FIG. 2 is a side view of the present invention.
Figure 3:
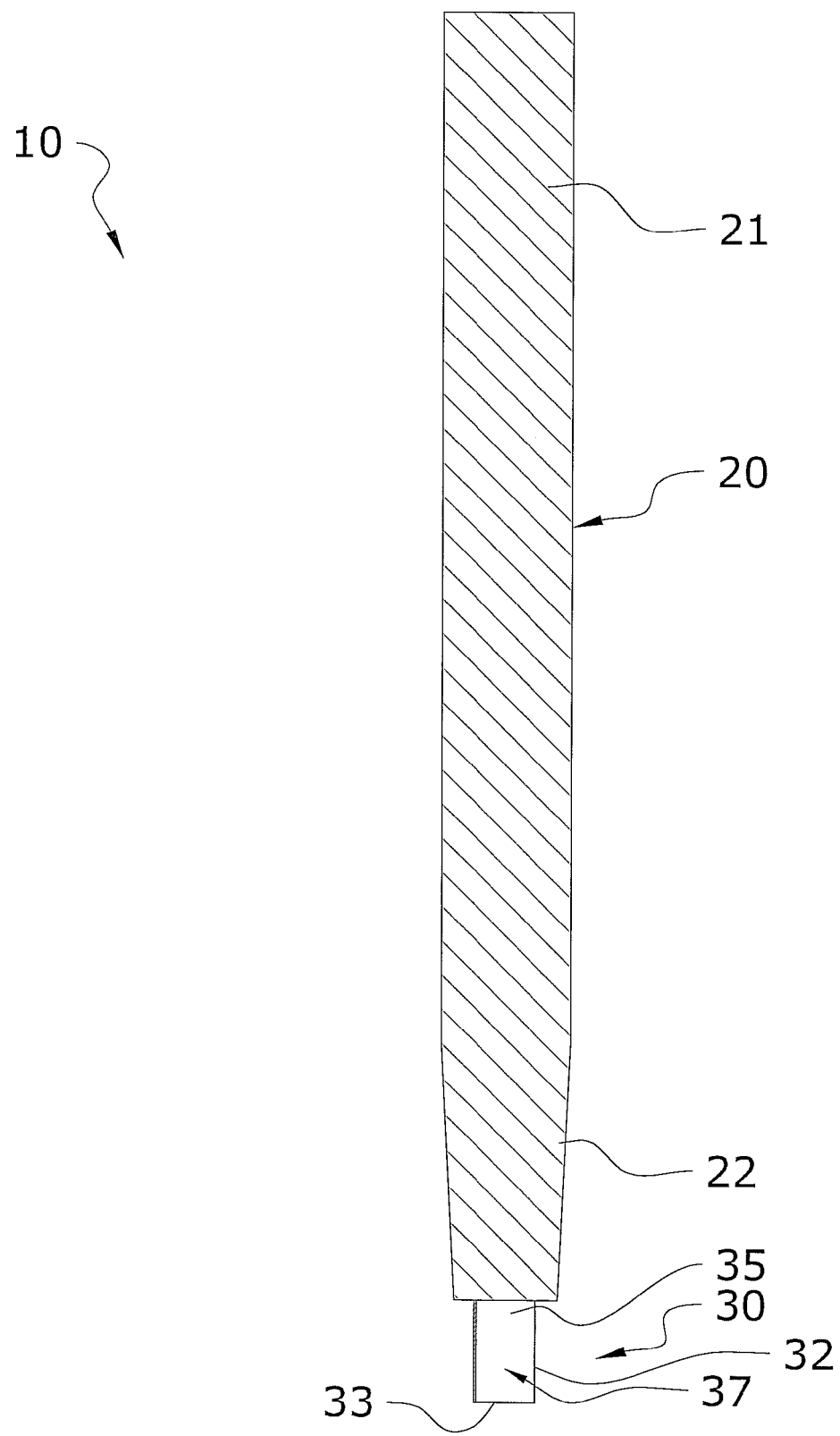
FIG. 3 is a sectional view of the blade taken along lines 3-3 of FIG. 2.
Figure 4:
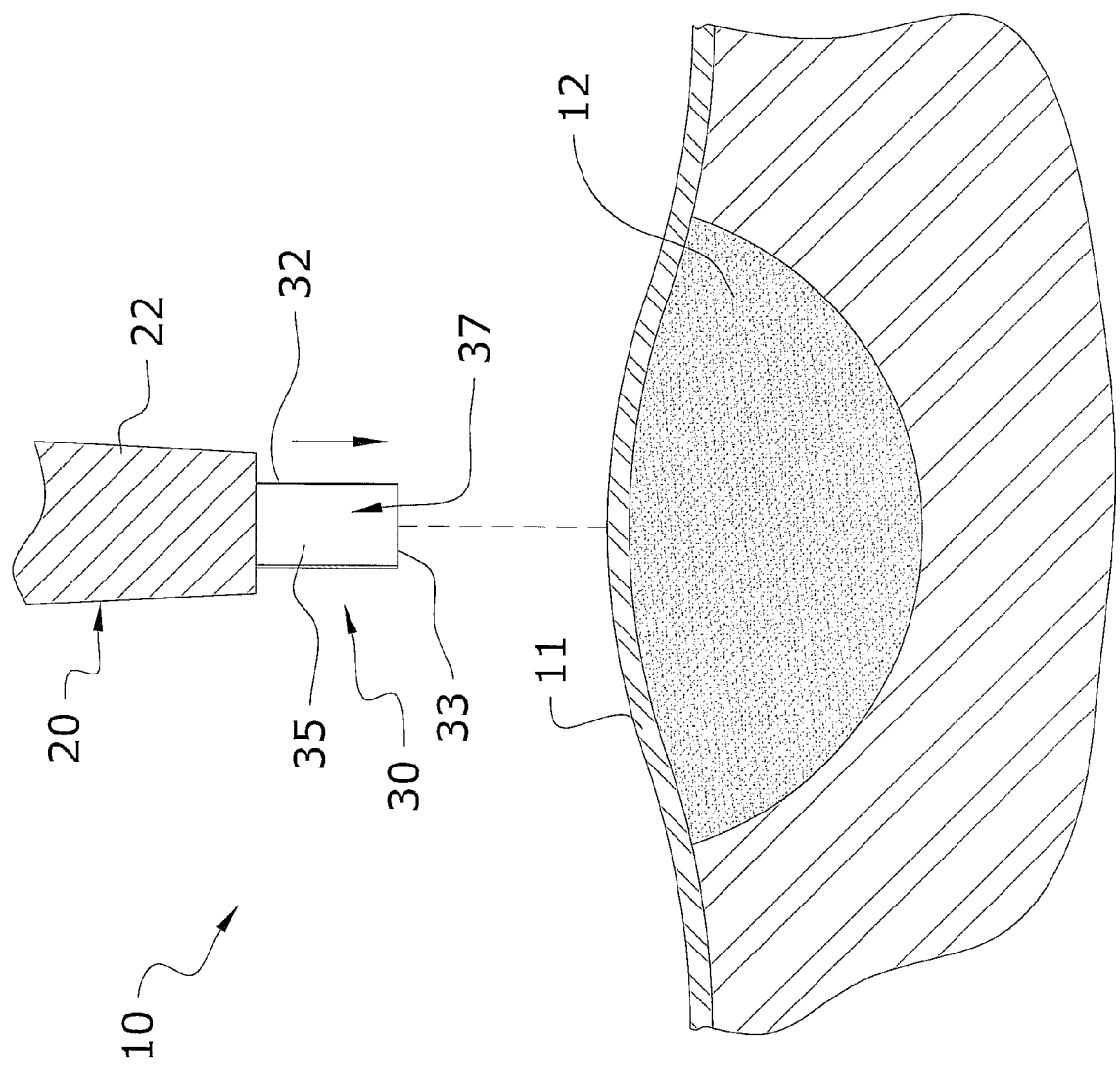
FIG. 4 is a sectional view of the apparatus aligned with the skin.
Figure 5:
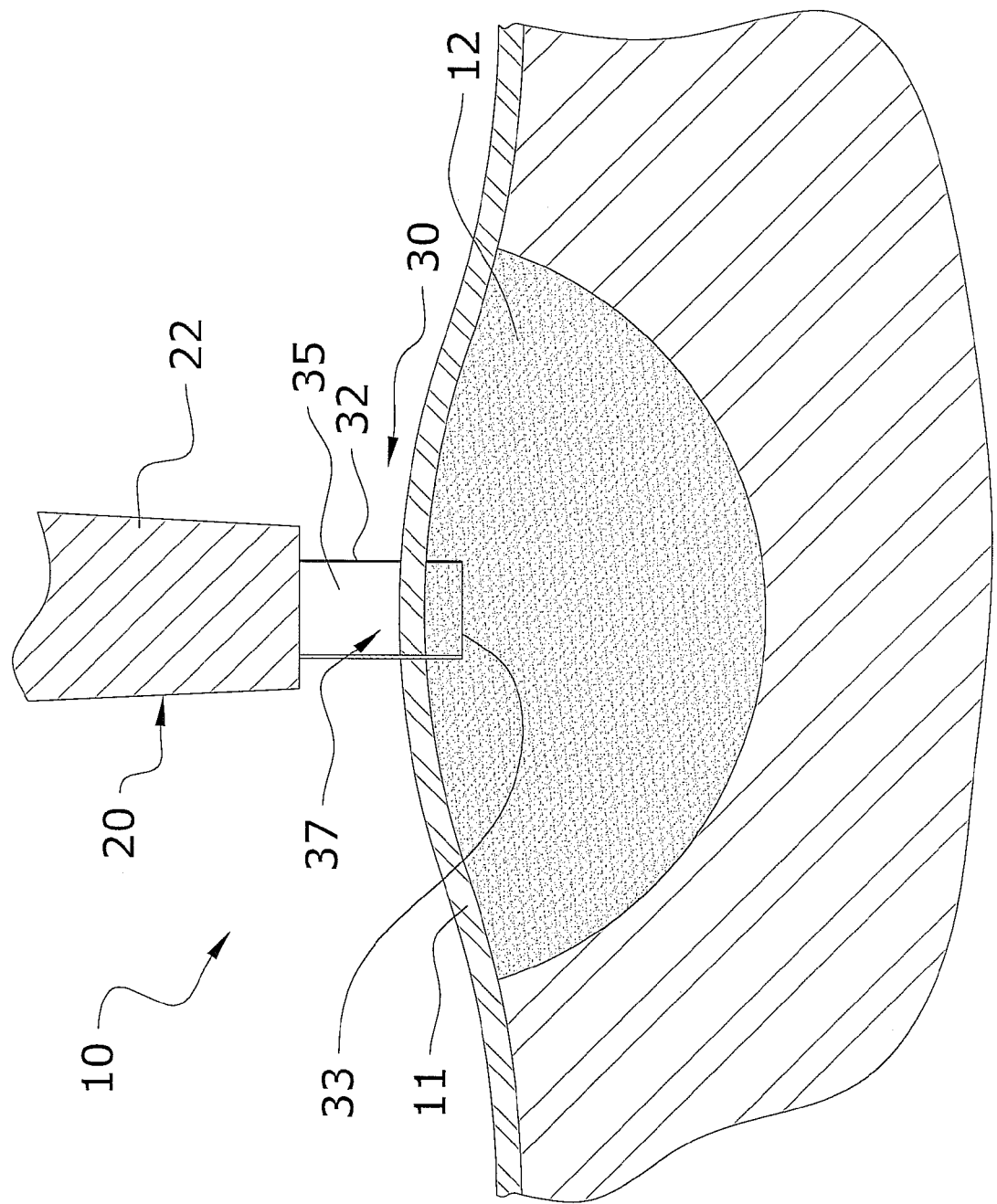
FIG. 5 is a sectional view of the apparatus forming a C-shaped incision within the skin to form the pivotal skin fragment.
Figure 6:
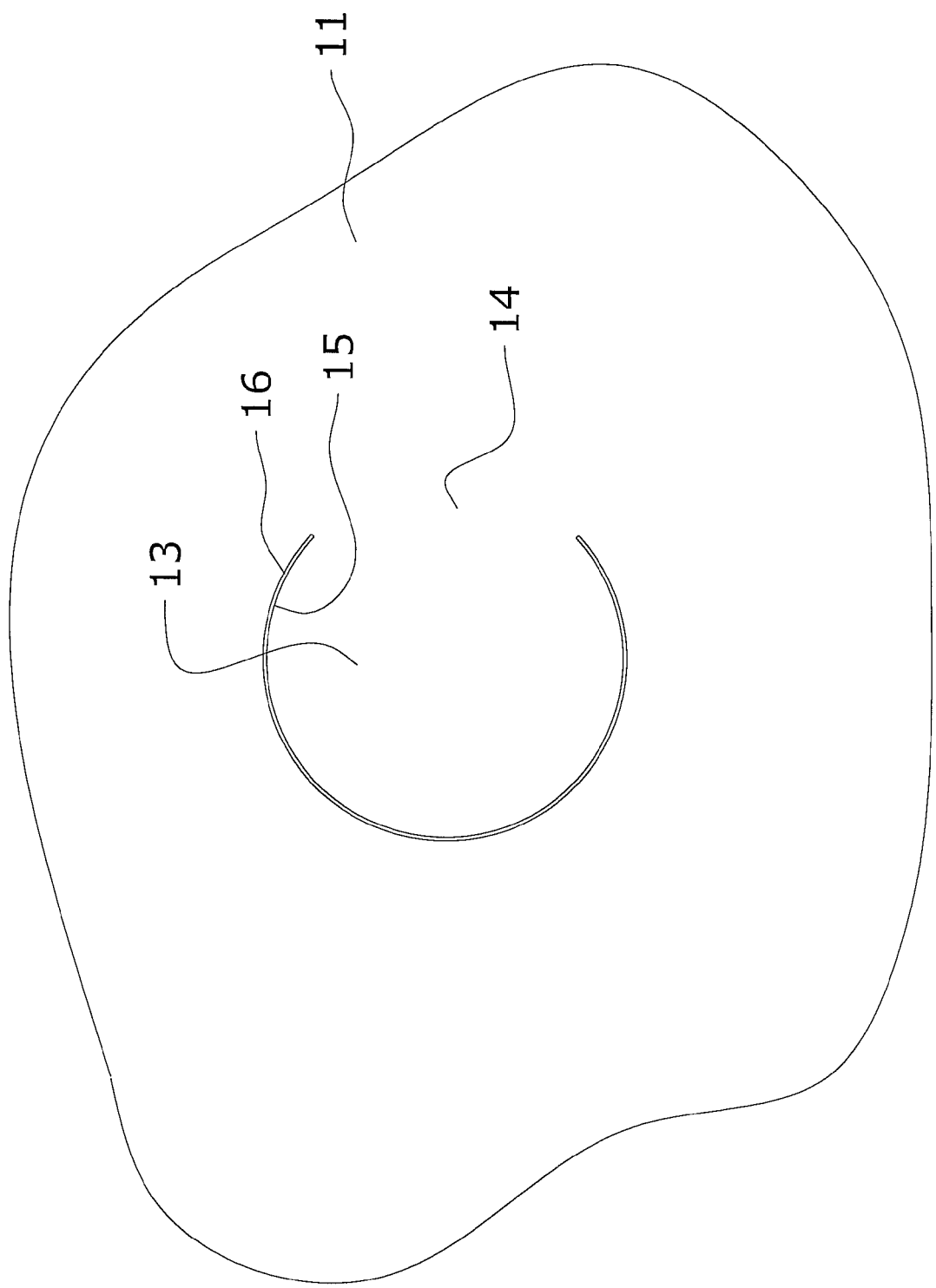
FIG. 6 is a top view of the formed C-shaped skin fragment.
Figure 7:
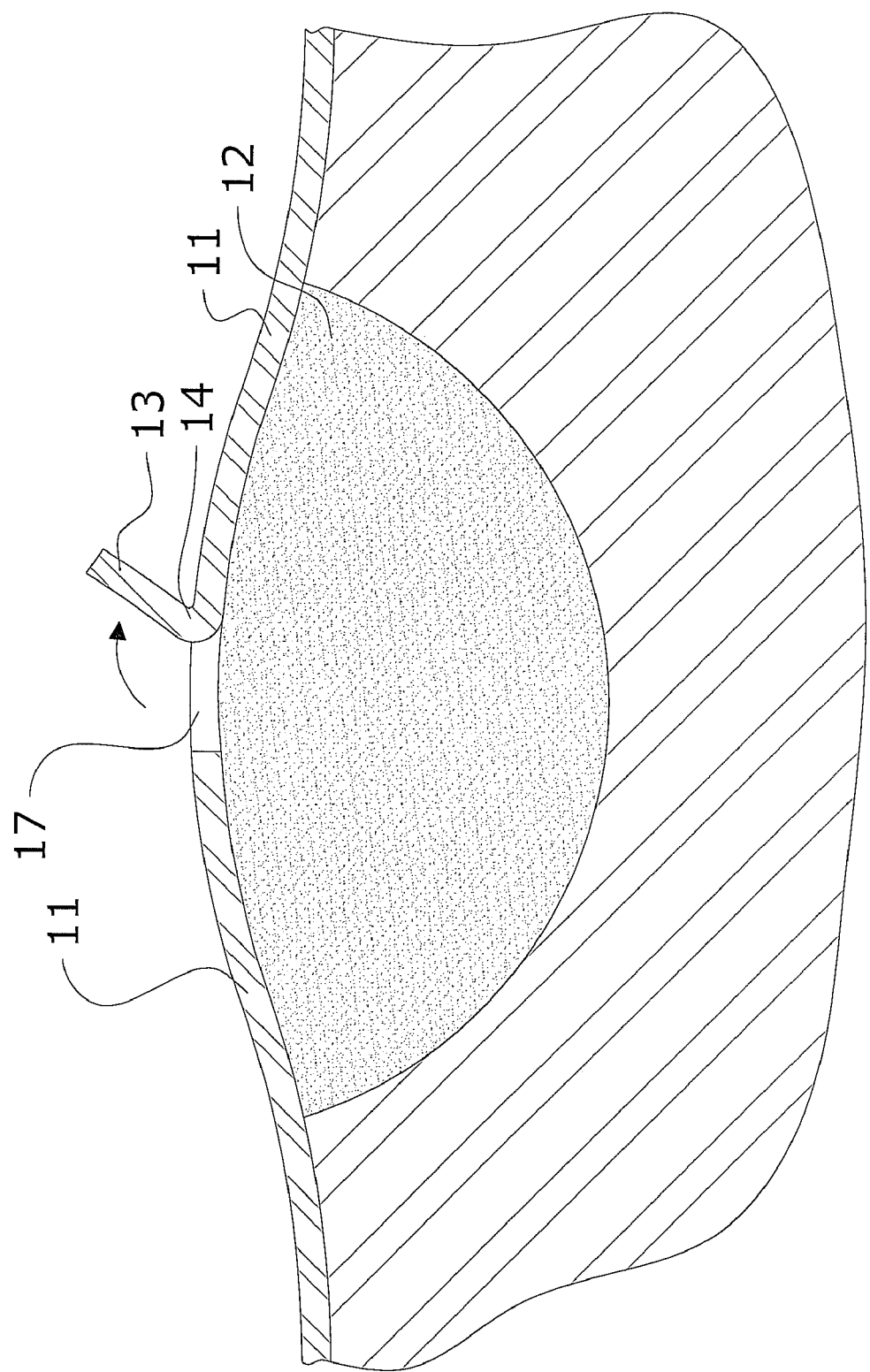
FIG. 7 is a sectional view of the skin fragment pivoted to an open position.
Figure 8:
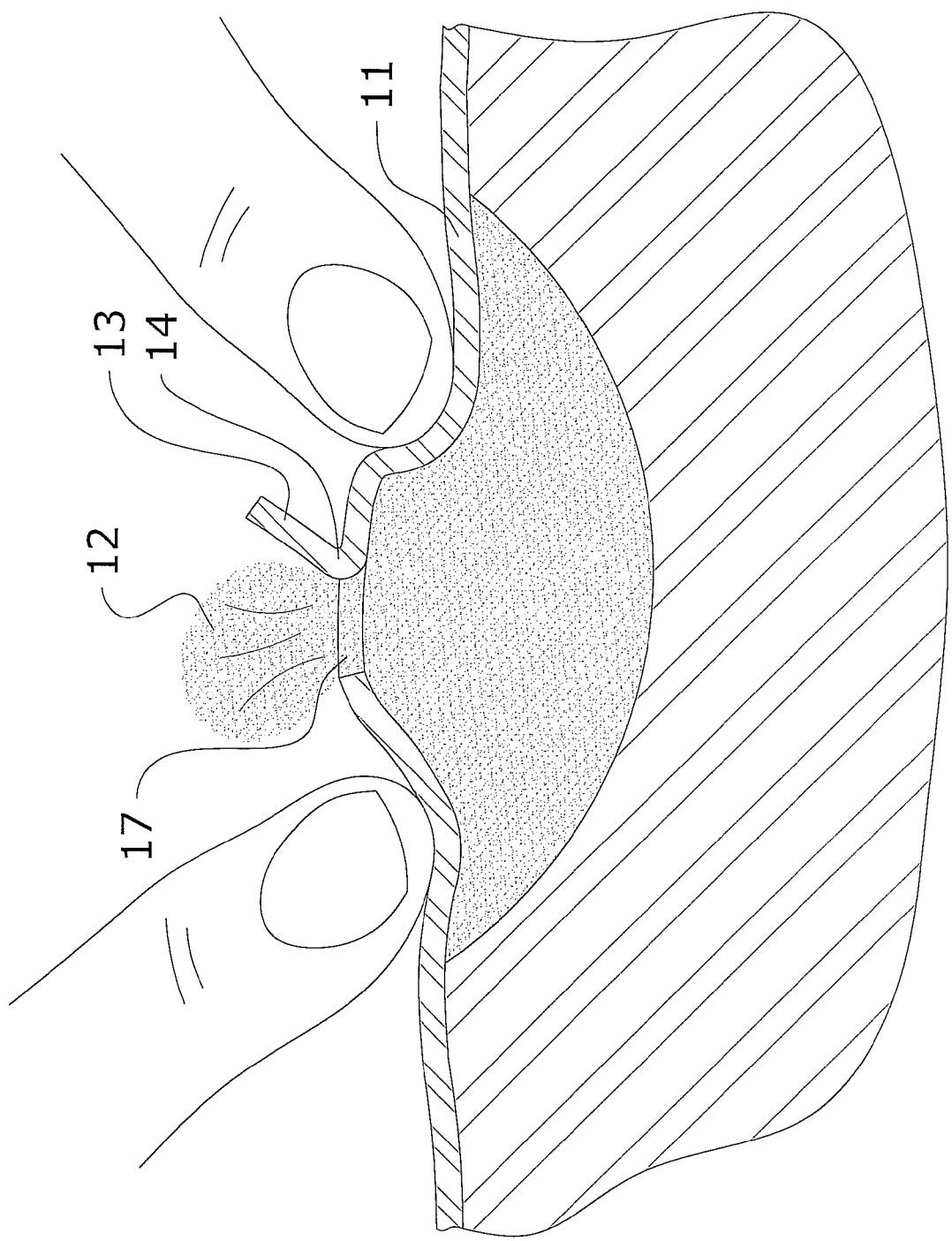
FIG. 8 is a sectional view of the subcutaneous material being removed through the formed opening by applying lateral pressure to the surrounding skin.
Figure 9:
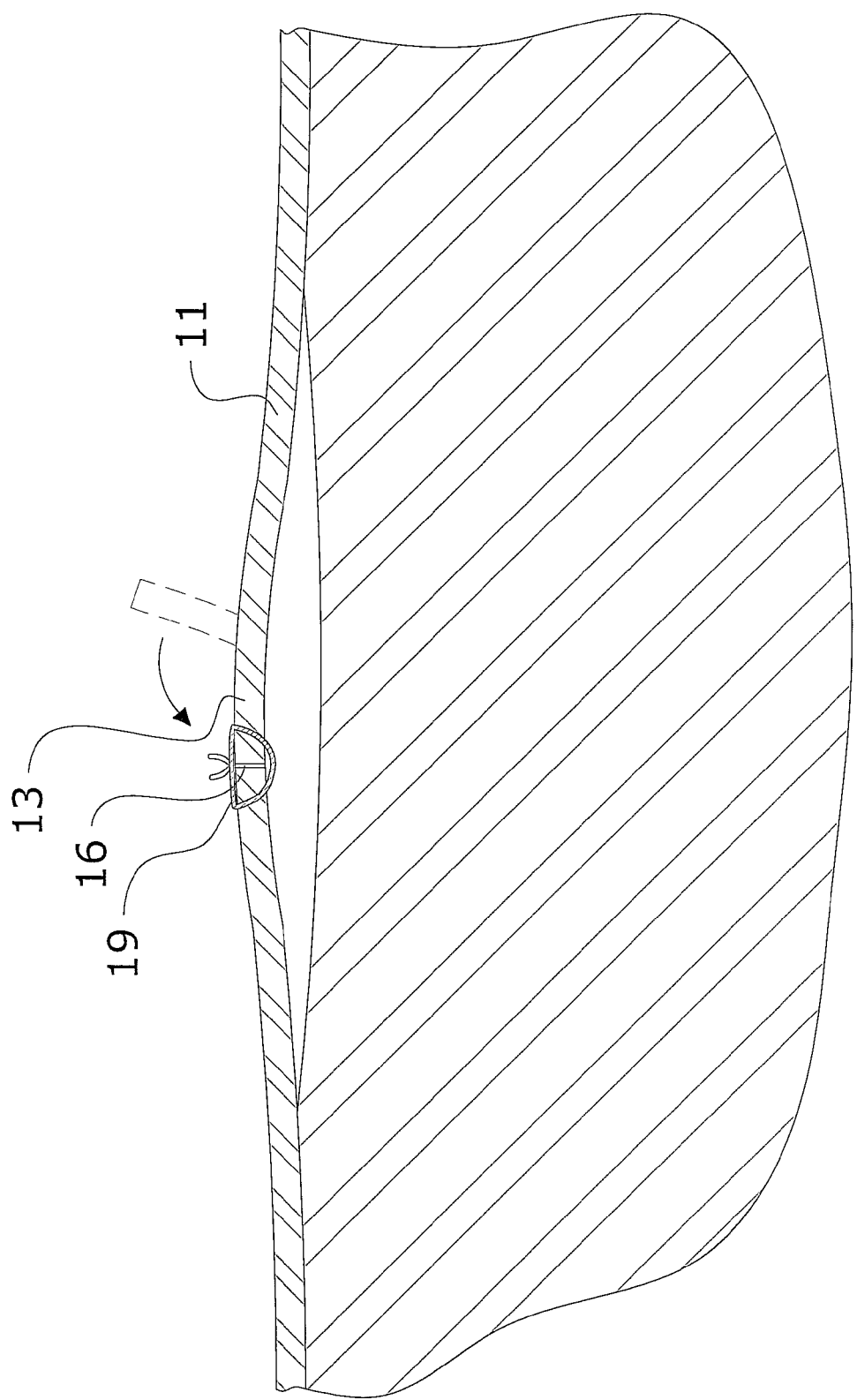
FIG. 9 is a sectional view of the skin fragment pivoted back over the opening to a closed position and connected to the surrounding skin.

Turning now descriptively to the drawings, in which similar reference characters denote similar elements throughout the several views, FIGS. 1 through 9 illustrate a surgical skin punch apparatus 10, which comprises an elongated handle 20 and a cutting member 30 including a plurality of cutting edges 31, 32, 33, wherein the cutting member 30 extends from the elongated handle 20. The cutting member 30 is comprised of a C-shape to form a pivotal skin fragment 13 to access subcutaneous material 12 beneath. A method of using the apparatus 10 is also described.

B. Handle

The handle 20 is comprised of a rigid and elongated configuration suitable for a physician to grasp easily and maneuver to perform the surgical procedure. The handle 20 may be comprised of various materials, such as but not limited to metal or plastic. In the preferred embodiment, the handle 20 has a length of approximate 8 centimeters and a diameter of approximately 8 millimeters; however other sizes of handles 20 may be appreciated. The handle 20 is also preferably hollow to provide a lightweight structure; however the handle 20 may be solid in alternate embodiments.

The handle 20 generally includes a first section 21 and a second section 22. The second section 22 extends from the first section 21 in an integral manner. The first section 21 is generally comprised of a uniform first diameter. The second section 22 is generally comprised of an inwardly tapered second diameter. The second diameter thus tapers to a smaller width than the first diameter to allow the physician to comfortable grasp the second section 22 which allows for easy maneuvering of the handle 20 and apparatus 10 during use. The second section 22 is also generally shorter than the first section 21.

C. Cutting Member

The cutting member 30 extends from the handle 20 on an end adjacent the second section 22. The cutting member 30 is used to cut through the skin of the patient so that the desired material 12 underneath the skin may be removed. The cutting member 30 is also able to cut the skin in a maimer so that the skin fragment 13 left resembles a flap not completely detached from the surrounding skin 11 so that after the surgical procedure is finished the fragment 13 may be simply pivoted back over the wound site and opening 17 and reattached to the surrounding skin 11 via a stitch 19, etc.

The cutting member 30 achieves the ability to the cut the skin so as to leave a skin fragment 13 via being comprised of a C-shape or crescent shape. The cutting member 30 is also elongated to extend through the multiple layers of the skin and is generally cylindrical in shape minus the slot 35 removed to form the C-shape. The C-shaped cutting member 30 is also preferably concentric with the handle 20 and extends along a center longitudinal axis of the handle 20. The cutting member 30 may be comprised of various materials, such as but not limited to stainless steel.

The elongated structure of the cutting member 30 defines a hollow cavity 37 extending within to receive the portion of the skin fragment 13 and subcutaneous material 12 inside of the perimeter of the cutting member 30 when forming the incision 16. The cavity 37 is generally cylindrical in shape and in fluid communication with the slot 35 so as to leave the skin fragment 13 pivotally connected to the surrounding skin 11.

The C-shaped of the cutting member 30 also defines a first cutting edge 31, a second cutting edge 32, and a third cutting edge 33. The first cutting edge 31 and the second cutting edge 32 define the slot 35 between thereof that receives the portion 14 of the skin fragment 13 left uncut. The first cutting edge 31 and the second cutting edge 32 are parallel to each other and to the longitudinal axis of the handle 20 and cutting member 30.

The slot 35 and cutting member 30 generally have a ratio of 1:3 in surface area, wherein approximately one-fourth of the surface area of a complete cylindrical cutting member is missing because of the existence of the slot 35 and wherein the slot 35 comprises at least 25% of a circular perimeter around the cutting member 30 in a cross-sectional manner. It is appreciated that the slot 35 may comprise 30-40% of the perimeter around the cutting member 30.

The third cutting edge 33 forms the outer face of the cutting member 30 to initially engage the skin surface when making the incision 16. The third cutting edge 33 is comprised of a C-shape and is parallel to the first cutting edge 31 and the second cutting edge 32. The first cutting edge 31, the second cutting edge 32 and the third cutting edge 33 are all preferably razor sharp to easily pierce the skin of the patient.

D. Operation of Preferred Embodiment

In use, after disinfecting and injecting anesthesia upon the area over the subcutaneous tumor or other abnormality the cutting member 30 of the apparatus is pushed downwards with very little or no rotating movement (less than 1 mm clockwise and anti-clockwise rotation). The cutting member 30 is pushed completely through the skin surface being perpendicular to the skin surface.

Pushing the cutting member 30 completely through the skin surface causes a skin fragment 13 of a flap-like form to be created, wherein a first portion 14 of a perimeter of the skin fragment 13 is connected to the surrounding skin 11 and a second portion 15 of the perimeter of the skin fragment 13 is disconnected from the surrounding skin 11. The skin fragment 13 is pivoted back over the first portion 14 of the perimeter thus exposing an opening 17 to allow better access to deeper subcutaneous material 12.

The subcutaneous material 12 (e.g. tumor, etc.) is fragmented by a blunt scissors then evacuated with lateral pressure by the hands of the surgeon or assistant. It is appreciated that since the skin fragment 13 is not completely removed from the surrounding skin 11 blood is able to continually flow the skin fragment 13 during the surgical procedure and thus keep the skin fragment 13 healthy and living.

The skin fragment 13 is then pivoted back over the opening 17 thus closing the wound and opening 17. The skin fragment 13 may then be sutured to the surrounding skin 11 around the perimeter of the skin fragment 13 that was cut from the surrounding skin 11 with a single stitch 19 or various other fasteners. The skin fragment 13 is reconnected to the surrounding skin 11 in a flush and even manner that will allow for easy blood flow to the skin fragment 13 from the surrounding skin 11 because of the first portion 14 of the skin fragment 13 that was left uncut due to the C-shaped cutting member 30.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A surgical skin punch apparatus, comprising:
   an elongated handle; and
   a cutting member, wherein said cutting member extends from said elongated handle;
   wherein said cutting member is comprised of a cross-sectional C-shape to form a pivotal skin fragment to access material beneath, and further configured to leave a flap of skin; wherein said cutting member includes a slot to form said cross-sectional C-shape, wherein said slot comprises between 25% and 40% of a circular perimeter around said cutting member; wherein the C-shaped cutting member is concentric with the handle and extends along a center longitudinal axis of the handle.

2. The apparatus of claim 1, wherein said cutting member is comprised of an elongated structure.

3. The apparatus of claim 1, wherein said cutting member is hollow.

4. The apparatus of claim 1, wherein said elongated handle is hollow.

5. The apparatus of claim 1, wherein said elongated handle is comprised of a uniform diameter.

* * * * *